(12) United States Patent
Tagliani et al.

(10) Patent No.: US 8,067,195 B2
(45) Date of Patent: Nov. 29, 2011

(54) PROCESS FOR PRODUCING 7-METHOXY-3-DESACETYLCEFALOTIN

(75) Inventors: Auro Roberto Tagliani, Pavia (IT); Gabriele Guastalegname, Galgagnano (IT); Giovanni Fogliato, Barzano (IT); Riccardo Monguzzi, Dorio (IT)

(73) Assignee: ACS Dobfar S.p.A., Tribiano (IT)

( * ) Notice: Subject to any disclaimer, the term of this patent is extended or adjusted under 35 U.S.C. 154(b) by 405 days.

(21) Appl. No.: 12/192,467

(22) Filed: Aug. 15, 2008

(65) Prior Publication Data

US 2009/0093032 A1  Apr. 9, 2009

(30) Foreign Application Priority Data

Oct. 9, 2007 (IT) ............... MI2007A1951

(51) Int. Cl.
*C12P 35/00* (2006.01)

(52) U.S. Cl. ....... 435/47; 435/252.1; 435/118; 435/130; 435/170

(58) Field of Classification Search .............. 435/47, 435/118, 130, 170, 252.1
See application file for complete search history.

(56) References Cited

U.S. PATENT DOCUMENTS

| 4,297,488 A | 10/1981 | Christensen et al. | |
|---|---|---|---|
| 4,474,879 A * | 10/1984 | Heiney | 435/47 |

FOREIGN PATENT DOCUMENTS

GB 1121308 7/1968

OTHER PUBLICATIONS

Kotz et al. "Chemistry & Chemical Reactivity" second eidtion. (1991) (Saunders College Publshing: Ft. Worth, TX), p. 149.*
Rawn, J. David "Biochemistry" (1983) (Harper & Row, Publishers: New York, NY), p. 50.*
Liras, P. Antonie van Leeuwenhock (1999) 75: 109-124.*
Ronald W. Ratcliffe, et al., "Total Synthesis of β-Lactam Antibiotics III. (+/−)-Cefoxitin", Tetrahedron Letters No. 46, XP-002413258, 1973, pp. 4653-4656.
Akio Takimoto, et al., "Batch production of deacetyl 7-aminocephalosporanic acid by immobilized cephalosporin-C deacetylase", Appl Microbiol Biotechnol, vol. 65, XP-002595997, 2004, pp. 263-267.
Michael Politino, et al., "Purification and Characterization of a Cephalosporin Esterase from *Rhodosporidium toruloides*", Applied and Environmental Microbiology, vol. 63, No. 12, XP-002177393, Dec. 1997, pp. 4807-4811.
Irene Martinez-Martinez, et al., "A colorimetric assay for the determination of acetyl xylan esterase or cephalosporin C acetyl esterase activities using 7-amino cephalosporanic acid, cephalosporin C, or acetylated xylan as substrate", Analytical Biochemistry, vol. 369, No. 2, Sep. 5, 2007, pp. 210-217.
J. D'A. Jeffery, et al, "Deacetylcephalosporin C", J. Biochem., vol. 81, XP-002595999. 1961, pp. 591-596.
Extended Search Report issued Sep. 2, 2010 in European Application No. 08162293.8.

* cited by examiner

*Primary Examiner* — Susan Hanley
(74) *Attorney, Agent, or Firm* — Oblon, Spivak, McClelland, Maier & Neustadt, L.L.P.

(57) ABSTRACT

The invention relates to a method for preparing 7-methoxy-3-desacetylcefalotin by a hydrolysis process which takes place in water and is catalyzed by an enzyme obtained from *Bacillus pumulis* possessing acetyl hydrolasic activity.

5 Claims, 2 Drawing Sheets

PROCESS FOR PRODUCING 7-METHOXY-3-DESACETYLCEFALOTIN

FIELD OF THE INVENTION

The present invention relates to a method for producing 7-methoxy-3-desacetylcefalotin (I),

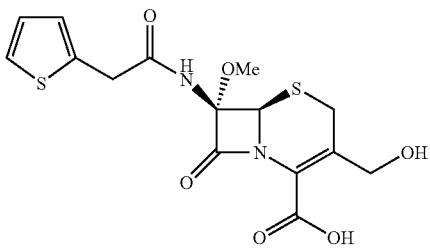

a cefoxitin synthesis intermediate, in accordance with an innovative process using a biocatalyst.

Cefoxitin pertains to the class of cephamycins, i.e. β-lactam antibiotics characterised by the presence of a methoxy group in position 7 of the cephalosporanic ring.

BACKGROUND OF THE INVENTION

This antibiotic is described in U.S. Pat. No. 4,297,488, which illustrates different synthesis paths comprising carbamoylation of various desacetylated intermediates with various agents, using different protective groups on the carboxyl and/or on the amino group. It also describes the passage of enzymatic hydrolysis to produce certain of these derivatives, using acetil-esterase from citrus fruit peel, although with very slow reactions (6-15 hours) and without commenting on the quality of the products obtained. A similar process is also described by the same authors in Tetrahedron Lett 46, 4653-6 (1973), using protected intermediates such as p-nitrobenzyl esters, on which a deprotection and an enzymatic hydrolysis are carried out, to hence obtain 7-methoxy-3-desacetylcefalotin in carboxylic acid form. The product is then treated with chlorosulphonyl isocyanate to obtain cefoxitin.

The synthesis paths generally used on an industrial scale in modern chemistry produce optically pure cefoxitin, using 7-ACA (7-aminocephalosporanic acid) as raw material, and comprise four main steps, preferably carried out in the following order:

1. acylation of the amino group in position 7
2. introduction of the methoxy group in position 7α
3. removal of the acetyl group in position 3
4. carbamoylation of the hydroxyl group in 3 obtained in the preceding step.

Step 1 corresponds to the synthesis of cefalotin, a cephalosporin. This is then transformed into the corresponding cephalomycin by methoxylation to give the intermediate II (step 2):

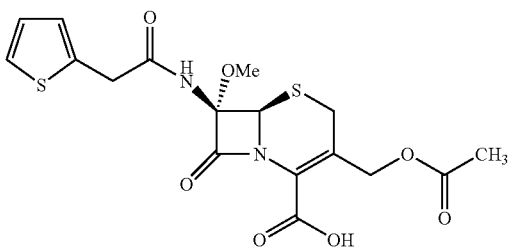

and then desacetylated to give the compound I.

Although other sequences are possible, the aforedescribed is advantageous as it does not use protective groups either for the amino group or for the carboxyl group, and hence enables the number of necessary operations to be minimized, while enabling a raw material saving.

For example WO2004/083217A1 (page 6) describes the saponification of the intermediate II with sodium hydroxide in a water-methanol mixture cooling to −45° C.; this temperature is maintained for the entire duration of hydrolysis, and can be raised only on termination of the reaction, after neutralizing the base with acid.

The compound I is then isolated as the benzathine salt, after removing the methanol by distillation at moderate temperature; it is thus evident that 1) the use of methanol is justified by the need to reach very low temperatures for the reaction and 2) it is necessary to remove the solvent before isolating the product.

Alternatively the product can be extracted in solvent either in the undissociated form by acidification, or as a basic salt, for example tetrabutylammonium, as described in EP 1748049A2.

Cefoxitin can be obtained from the compound I by carbamoylation of the isiocyanate group, as described in the aforesaid patents, or with other isocyanates, as described for example in U.S. Pat. No. 4,292,427.

In all cases, given the lability of β-lactam structures and the need to operate under extremely basic conditions, the desacetylation of compound I to give compound II is conducted at very low temperature to prevent product degradation; consequently organic solvents are used to lower the freezing point of the solutions.

These are therefore methods requiring the cooling of thousands of liters of solutions to a temperature of the order of −45° C., these temperatures to be maintained for the entire duration of the reaction, by using refrigeration machines or refrigerant fluids (such as liquid nitrogen); this results in a considerable energy cost. The solvent is then removed by distillation under vacuum by heating to +30/+40° C., with further considerable energy consumption (both for heating the solution and for the operation of the vacuum pump and condenser cooling).

It must also be considered that the use of solvents such as methanol involves danger due to solvent inflammability, possible operator intoxication, release of vapours into the environment, and drawbacks due to the production of methanol-containing aqueous effluents, which must be suitably disposed off.

A more ecocompatible path is therefore highly desirable, such as hydrolysis taking place only in water at ambient temperature. To effect such hydrolysis in a reasonable time and avoid product degradation a catalyst is required, for example an enzyme.

Enzymatic desacetylation of cephalosporins (not of cephamycins as in compound II) has been known for some time and has been described with enzymes of various origins.

For example acetyl esterase from wheat germ was described by Gilbert et al. in GB 1121308 (Glaxo, 1964), the enzyme present in citrus fruit peel was described by Jeffery et al in Biochem. J. 81, pages 591-6 (1961).

The aforesaid U.S. Pat. No. 4,297,488 describes the enzymatic hydrolysis of various cefoxitin synthesis intermediates, catalyzed by acetyl esterase from citrus fruit; however the method described therein is not applicable on an industrial scale, because of the poor performance of the catalyst. This is an enzyme of low specific activity involving very lengthy reaction times (6-15 hours described), difficult to produce as it derives from a poorly reproducible source subject to seasonal variations. Moreover it is applied in soluble form, is not recycled, and neither the purification nor the immobilization of the enzyme is described. Neither the yields of the acetyl derivatives obtained nor their quality are described.

Other enzymes active on cephalosporins have been discovered, starting from those involved in the biosynthesis path of cephalosporin C in *Acremonium chrysogenum* (or *Cephalosporium acremonium*) and in *Streptomyces clavuligerus*; these are considered as undesirable enzymatic activities, which lead to the formation of desacetyl cephalosporin C, a fermentation by-product. It should be noted that the biosynthesis of cephamycins in *Nocardia lactamodurans* and in *Streptomyces clavuligerus* does not comprise the hydrolysis of the acetyl group on a cephamycin (P. Liras, Antonie van Leeuwenhoek 75, 1999, pages 109-24); acetyl esterase activity on cephamycins is therefore not known, not even in cephamycin producer microorganisms.

Enzyme catalyzed hydrolyses of the acetyl group on 7-ACA or on cephalosporin C have been described, but not on cephamycins; in particular:

1) an esterase produced by *Bacillus subtilis* (Abbott and Fukuda, Antimicrob Agents Chemother 8, 3, pages 282-8, 1975 and Appl Microbiol, 30,3, pages 413-8 1975) is used in immobilized form for hydrolyzing 7-ACA to 3-desacetyl-7-ACA. The enzyme is sufficiently active and stable but tends to become detached from the immobilization support. Other authors (Takimoto et al. Appl Microbiol Technol 65, pages 263-7, 2004) describe the fermentation of this enzyme in recombinant *Eschericia coli*, its purification and immobilization on solid support and its use for producing 3-desacetyl-7-ACA.

2) The *Rhodosporidium toruloides* described by Politino et al. in Appl Environm Microbiol 63, 12, pages 4807-11, 1997, produces an enzyme active on 7-ACA, which can be used as catalyst in this reaction both in the form of a non-fermenting biomass (resting cells) and as an isolated and purified enzyme. The hydrolytic activity manifested by this enzyme on cefalotin is however low, only 34% of that on 7-ACA; Hydrolysis of cephamycins is not described. The same enzyme is also used by Chiang et al. (US 2002/0048781BMS, 2002) who describe a strain of recombinant *Acremonium crysogenum*, able to express acetyl esterase from Rhodosporidium, used to produce desacetylcephalosporin C directly in fermentation broths.

3) Another acetyl esterase is described by Venturi et al. in Appl Environ Microbiol 64, 2, pages 789-92, 1998: this is a xylan esterase produced by *Bacillus pumilus*, an enzyme connected with the degradation of xylans, which also shows activity on 7-ACA and on cephalosporin C; other publications describe expression of the same enzyme in coli. Activity on cephamycins is not described.

Hence enzymatic hydrolysis of the acetyl group of cephamycins has never been applied on an industrial scale in the state of the art; moreover, notwithstanding the wide literature available on a similar reaction in cephalosporins, an enzyme has not been described which is sufficiently active and stable for use on cephamycins.

SUMMARY OF THE INVENTION

An aspect of the present invention is a method for preparing the compound of formula I in which a compound of formula II is subjected to hydrolysis of the acetyl group, characterised in that said hydrolysis is conducted in water in the presence of a biocatalyst consisting of at least one enzyme possessing acetyl-hydrolasic activity, at a temperature between $-10°$ C. and $+45°$ C. (preferably between $0°$ C. and $+20°$ C.), at pH between 5 and 9 (preferably between 6 and 8), and finally separating the enzyme from the reaction medium by known methods.

In particular, this biocatalyst can be obtained from microorganisms chosen from the group consisting of Rhodosporidium toruloides, *Bacillus pumilus, Escherichia coli, Acremonium chrysogenum*, and *Streptomyces clavuligerus*, and can be presented in the form of free protein or immobilized on a solid support, or can consist of the microbic cells themselves. On termination of the reaction the biocatalysts can be separated and reused, while the compound I can be isolated from the aqueous solution by precipitation as the salt of an organic base or by extraction in solvent. It has been found that, preferably, said organic base is selected from the group consisting of benzathine and its salts.

Compared with the state of the art, the new method presents various advantages which can be summarized as follows:

greater working safety, by avoiding the use of harmful solvents (e.g. methanol) and strongly caustic solutions (e.g. sodium hydroxide), considerable energy saving by working at ambient temperature, so avoiding the considerable energy consumption necessary to reach and maintain the low temperatures generally used in these cases (e.g. less than $-45°$ C.), greater process productivity, by avoiding solvent distillation under vacuum, a working step which requires considerable time.

A product is obtained which is of quality equal to or greater than that obtainable by the procedures known up to the present time.

DETAILED DESCRIPTION OF THE INVENTION

Figure 1:
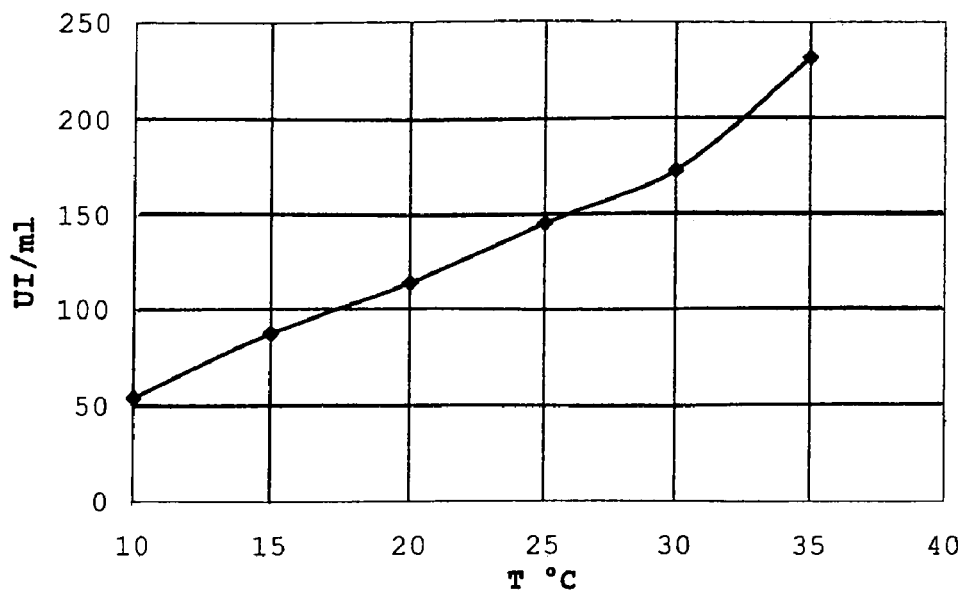
FIG. 1 Acetylesterase activity as a function of temperature.

The intermediate II can be prepared starting from cefalotin, a commercially available raw material of good quality and low price; the same cefalotin can be produced from 7-ACA by known methods. The methoxylation reaction is conducted at very low temperature, using a chlorinating agent and sodium methoxide and operating by known methods. On termination of the reaction the compound II can be isolated as a salt, either of alkaline metals or of organic bases, or can be extracted in water in the form of carboxylate.

A convenient synthesis path is described in WO2004/083217, Example 1, step i.

For the enzymatic desacetylation various catalysts were used, prepared by known methods or as described in the following examples.

The reaction product (compound I) was isolated as the benzathine salt, as described in WO2004/083217, or extracted in organic solvent, either a) as acid in undissociated form, or b) as tetrabutylammonium salt, following the procedure described in EP 1748049A2.

Cefoxitin was obtained from the compound I by reaction with chlorosulphonyl isocyanate, operating by known methods, to obtain a good quality product suitable for use as a drug.

The process is illustrated in the following examples, which however are to be considered as non-limiting.

Example 1

Chemical synthesis of
7-methoxy-3-desacetylcefalotin 300 g of 7-methoxy cefalotin in cyclohexylamine salt form (solution A), prepared by known procedures and having a titre of about 69% as acid, equal to about 500 mmoles, are added to a mixture of 1.0 liters of water and 1.15 liters of methanol. The mixture is cooled to −37° C.

Separately, a solution of 160 g of 30% sodium hydroxide in water in 300 ml of water is prepared and cooled to +5° C., them poured slowly into solution A, while maintaining the temperature between −45/−35° C. for about one hour after finishing the addition. The reaction kinetics are monitored by HPLC analysis: when the residual 7-methoxy cefalotin is less than 0.7 g/l the reaction is interrupted by adding 90 g of 80% acetic acid while maintaining the temperature within −5° C. The pH, which must be neutral, is monitored, correcting to 6.8-7.0 if necessary. The mixture is distilled under vacuum by heating to +30/+35° C., until a concentration of about 100 g/l of 7-methoxy-3-desacetylcefalotin is obtained, after which decolorization with carbon is applied. The volume is diluted to about 1.9 liters to achieve a concentration of about 80 g/l, then 300 ml of ethyl acetate and 130 g of benzathine diacetate are added, adding a little solid product to trigger the precipitation. The mixture is cooled to 0/+5° C. and the temperature maintained until a product concentration in the mother liquors of less than 10 g/l is achieved, after which it is filtered through a Buchner funnel. The solid is washed with water and then with ethyl acetate, after which it is mashed in an ethyl acetate 85%/acetone 15% mixture to achieve an anhydrous product.

About 208 g of 7-methoxy-3-desacetylcefalotin benzathine salt are obtained, of titre about 70% as acid, equal to 380 mmoles, for a molar yield of 76%.

Example 2

Enzymatic hydrolysis of
7-methoxy-3-desacetylcefalotin with
*Rhodosporidium toruloides* biomass

*Rhodosporidium toruloides* ATCC 10657 is grown in a flask or fermenter for 72 hours from inoculation as described in the literature, withdrawing whole broth samples for monitoring the quantity of acetyl esterase produced. The enzymatic activity is expressed in international Units (IU), equal to the micromoles of substrate converted per minute, and is determined by hydrolysis of 7-ACA (20 g/l in water); the reaction is temperature controlled at +25° C. and pH-controlled at 6.5 by adding 0.1M NaOH by automatic titration (pH-stat, Crison Instruments SA, Barcelona, Spain). The growth broth is centrifuged at 10000 r.p.m. for 15 minutes, the pellet is resuspended in phosphate buffer and again centrifuged, to obtain a paste of wet cells with specific activity of about 6-10 IU per gram.

40.8 g of 7-methoxy cefalotin cyclohexylamine salt are dissolved in about 250 ml of water, correcting the pH to 7.0 with 3N ammonium hydroxide. The titrator is set to maintain pH 7.0, temperature is controlled at +20° C. and 50 g of Rhodosporidium cell paste are added. After about 1 hour 30 minutes the reaction is complete, the cells are separated by centrifugation to obtain about 340 ml of 7-methoxy-3-desacetylcefalotin solution, which is decolorized with carbon and filtered through paper. 55 ml of ethyl acetate and 17.7 g of benzathine diacetate are added, the product being isolated as described in Example 1.

28 g of 7-methoxy-3-desacetylcefalotin benzathine salt are obtained, of titre about 70% as acid, equal to 51 mmoles, molar yield of 77%.

The *Rhodosporidium* cells can be reused for various hydrolysis cycles.

Example 3

Enzymatic hydrolysis of
7-methoxy-3-desacetylcefalotin with acetyl-esterase
from *Rhodosporidium toruloides*

The *Rhodosporidium toruloides* biomass obtained as described in Example 1 is lysed by treatment with EDTA (ethylenediaminotetraacetic acid), to obtain an aqueous solution containing the acetyl esterase activity, which is purified by chromatography with carboxymethyl Sepharose, following the procedures known in the literature (Politino et al, *Appl. Environ. Microbiol.* 63, 12, pagg. 4807-11, 1997).

870 g of 7-methoxy-cefalotin benzathine salt prepared as in Example 1 are dissolved, the pH is corrected to 7.0 and the volume diluted to a total of 6000 ml, then 200 ml of a solution of acetyl esterase are added and the pH maintained at 7 by automatic titration with 3N ammonium hydroxide. On termination of the reaction the enzyme is separated from the product by ultrafiltration using the Millipore ProScale apparatus with Nanomax membrane and 10000 Da cut-off. From the permeate, about 5 liters of a solution of 7-methoxy-3-desacetylcefalotin are obtained, which is isolated as described in Example 1, while the concentrate containing the enzyme is reused for the next hydrolysis cycle. The compound I is isolated as described in Example 1.

Example 4

Enzymatic hydrolysis of
7-methoxy-3-desacetylcefalotin with recombinant
*Escherichia coli* biomass The enzyme acetyl xylan esterase from *Bacillus pumilus* was expressed in recombinant *Escherichia coli* obtained by the procedures described by Venturi et al. in Microbiology 146, pages 1585-91 (2000).

The 7-methoxy-cefalotin was hydrolyzed as described in Example 3, using 340 g of *E. coli* biomass as catalyst; on termination of the reaction the 7-methoxy-3-desacetylcefalotin solution was separated by ultrafiltration, isolating the product in the form of benzathine salt as described in Example 1.

The ultrafiltration retentate is a suspension of partially lysed coli cells and free enzyme, which can be reused in subsequent cycles.

Example 5

Enzymatic hydrolysis of
7-methoxy-3-desacetylcefalotin with acetyl-esterase
immobilized on epoxy resin The xylan esterase produced in recombinant coil as described in Example 4 was partially purified by destroying the cells with a cell disruptor press (Constant Systems Ltd.) at 1000 bar, then centrifuging at 20000 r.p.m. for 30 minutes. The supernatant thus obtained is dialyzed by ultrafiltration with a 10 KDa membrane ProScale Millipore apparatus then chromatographed on Sepharose Q Fast Flow resin as described in the literature (Venturi et al., *Microbiology* 146, pages 1585-91, 2000).

The partially purified enzyme was concentrated by ultrafiltration and then diluted with 10 volumes of a 1.2 M $K_2HPO_4$ solution at pH 8.0, then immobilized on the epoxy resin Sepabeads EC-EP (Diaion SpA, Mitsubishi) with a load of 120 IU per gram of resin. The resin suspension is agitated for 48 hours, then filtered through a Buchner funnel and washed with 10 volumes of water (10 ml per gram of resin); a solid catalyst is obtained having an activity of about 70 IU per gram.

100 g of 7-methoxy-cefalotin cyclohexylamine salt are dissolved in water to a total volume of 450 ml, then hydrolysis is carried out using as catalyst 66 g of immobilized enzyme, maintaining the pH constant at 7 by automatic titration with 3N ammonium hydroxide.

After 2.5 hours the reaction is complete, the enzyme is filtered through a sintered glass funnel and the 7-methoxy-3-desacetylcefalotin isolated by adding 50 g of benzathine diacetate and operating as described in Example 1.

69.6 g of product are obtained with titre 70.8% as acid 7-methoxy-3-desacetylcefalotin for a molar yield of 78%.

The catalyst can be reused for numerous reaction cycles.

Example 6

Enzymatic hydrolysis of 7-methoxy-3-desacetylcefalotin with acetyl-esterase immobilized on amino resin The enzyme acetyl esterase from *B. pumilis* produced in recombinant coli as described in Example 4 is purified as described in Example 5.

100 g of Sepabeads EC-HA resin (Diaion) are abundantly washed with water, then suspended in 100 ml of 0.2 M phosphate buffer at pH 7. 170 ml of 25% glutaraldehyde-in-water solution are added and left under agitation for 16 hours, then the purified enzyme solution is added to a total of 12000 IU. After 3 hours the mixture is filtered through a Buchner funnel, washing abundantly with water. A catalyst with activity 55 IU/gram is obtained.

Hydrolysis is conducted as described in Example 5, using 84 grams of immobilized acetyl-esterase. After three hours of reaction the enzyme is filtered off and the benzathine salt precipitated as described in Example 1. The product obtained is suspended in four volumes of isopropanol (weight/volume) and then filtered, to obtain 68 g of 7-methoxy-3-desacetylcefalotin benzathine salt of titre 70.5%, equal to a molar yield of 76%.

The catalyst can be reused for numerous reaction cycles.

Example 7

Enzymatic hydrolysis of 7-methoxy-3-desacetylcefalotin with acetyl-esterase immobilized on glyoxyl resin 100 g of Sepabeads EC-HA resin (Diaion) are abundantly washed with water, then 800 ml of a 0.05M sodium metaperiodate solution are added; after 1.5 hours the mixture is filtered through a Buchner funnel, with abundant washing with water. The resin is suspended in 700 ml of 50 mM bicarbonate buffer at pH 10, then 12000 IU of enzyme, purified as described in example 5, are added.

After one hour 1400 ml of a 1 mg/ml sodium borohydride solution in water are added, left to react for 30 minutes and then filtered through a porous baffle, with abundant washing with water. A catalyst with activity 38 IU/gram is obtained.

The hydrolysis reaction is conducted as described in Example 5; after 3.5 hours the reaction is interrupted and the product isolated. 65 g of 7-methoxy-3-desacetylcefalotin benzathine salt of titre 70% are obtained, equal to a molar yield of 73%.

The catalyst can be reused for numerous reaction cycles.

Example 8

Enzymatic hydrolysis of 7-methoxy-cefalotin from methylene solution

The cefalotin methoxylation reaction is conducted using N-chloro-succinimide and sodium methylate in methylene chloride and methanol, as described in WO2004/083217A1; after washing with aqueous solutions, an 82 g/l solution of acid 7-methoxy-cefalotin in methylene chloride is obtained.

500 ml of methylene solution are extracted with about 300 ml of water, titrating with a 10% (w/v) sodium carbonate aqueous solution to obtain a final pH of 8.0; the phases are separated, and the methylene phase is washed with a little water to obtain 355 ml of an aqueous 109 g/l product solution, equal to an extraction yield of 94%. The aqueous phase is distilled under vacuum at +25° C., to eliminate solvent residues.

The aqueous phase is hydrolyzed with 40 grams of enzyme described in Example 6, controlling the pH with a 10% (w/v) sodium carbonate aqueous solution; after two hours the reaction is interrupted and the product isolated.

33 g of 7-methoxy-3-desacetylcefalotin benzathine salt are obtained of titre 70.8%. The catalyst can be reused for numerous reaction cycles.

Example 9

Synthesis of Cefoxitin without Isolating Intermediates 7-methoxy-3-desacetylcefalotin is prepared as described in Example 8, to obtain an aqueous solution of concentration 80 g/l which is decolorized with 2 g of carbon; after filtration, solid NaCl is added until saturation and the solution extracted with a solution of tetrabutylammonium bromide in methylene chloride, following the procedure described in EP1748049A2. Carbomoylation is effected in tetrahydrofuran with chlorosulphonyl isocyanate, isolating acid cefoxitin which is then transformed into the corresponding sodium salt as described in the same patent.

13 g of sodium cefoxitin are obtained.

Example 10

Isolation of 7-methoxy-3-desacetylcefalotin as acid or sodium salt

The reaction is conducted as described in Example 6; on termination of hydrolysis the catalyst is filtered off and reused, and the aqueous solution is acidified until the 7-methoxy-3-desacetylcefalotin begins to precipitate, precipitation is allowed to continue for 30 minutes and then hydrochloric acid is added until pH 2.5, cooling to +4° C. The mixture is filtered through a Buchner funnel to obtain 7-methoxy-3-desacetylcefalotin as a white solid.

The mother liquors are extracted with ethyl acetate, the phases are separated and sodium 2-ethylhexanoate is added to the organic phase, to obtain precipitation of 7-methoxy-3-desacetylcefalotin sodium salt.

Example 11

Enzymatic hydrolysis of 7-methoxy-cefalotin in aqueous suspension 130 g of 7-methoxy cefalotin cyclohexylamine salt are suspended in 300 ml of water, then a 10% (w/v) sodium carbonate aqueous solution is added to pH 7; a suspension is obtained to which 100 g of immobilized enzyme are added, prepared as described in Example 6. The reaction is carried out under pH-stat conditions, temperature controlling at +20° C.; complete dissolution of the substrate is observed as hydrolysis proceeds. The procedure is continued until a 7-methoxy-cefalotin residue of less than 0.5 g/l is obtained, then the catalyst is filtered off and the product isolated as described in Example 1. 98.3 g of 7-methoxy-3-desacetylcefalotin benzathine salt are obtained of titre 70%, for a molar yield of 85%.

Example 12

Isolation of 7-methoxy-3-desacetylcefalotin by hot precipitation of its benzathine salt The reaction is conducted as described in Example 11. with the only difference that the water/ethyl acetate mixture is heated to +35° C. before adding the benzathine diacetate; on triggering precipitation of the 7-methoxy-3-desacetylcefalotin benzathine salt the temperature is maintained at +30/35° C. for about 30 minutes, with cooling gradually to +4° C. before filtering. A molar yield of about 85% is obtained.

Example 13

Use of benzathine for precipitating 7-methoxy-3-desacetylcefalotin

The reaction is conducted as described in Example 11. with the only difference that 10 vol % of methanol is added to the aqueous 7-methoxy-3-desacetylcefalotin solution, then ethyl acetate is added, heating to +30/35° C. before adding benzathine base. The mixture is cooled gradually to +4° C. before filtering. A molar yield of about 85% is obtained.

Similar results are obtained using ethanol, isopropanol or glycerine instead of methanol.

Example 14

Acetyl Esterase Activity as a Function of Temperature

A solution of ethyl acetate (0.5 ml) in 50 mM phosphate buffer at pH 7 (50 ml) is prepared, then hydrolysis is effected with 100 microliters of acetyl xylan esterase from recombinant *Bacillus pumilus* in *E. coli*, prepared as described in Example 5, using the free non-immobilized protein.

Various tests are conducted at constant pH by automatic titration, at temperatures from +10° C. to +35° C., calculating for each test the enzyme hydrolytic activity on the basis of the base addition rate during the first 10 minutes of reaction.

The activity is expressed in International Units (IU) per ml of solution by titrating with 0.1N NaOH the acetic acid quantity released by the ester hydrolysis, and is calculated by the formula:

IU=[mean NaOH consumption (ml/min)×100×*f*]/sample volume (ml)

where f=correction factor for the 0.1N soda titre
mean consumption=0.1N NaOH consumption during the first 10 minutes of titration, expressed in ml/min
sample volume=volume of acetyl esterase solution, expressed in ml.

By plotting the expressed enzymatic activity against reaction temperature the graph shown in FIG. 1 is obtained.

Similar results are obtained using the protein immobilized on resin as described in Examples from 5 to 7.

Example 15

Acetyl Esterase Activity as a Function of pH

Figure 2:
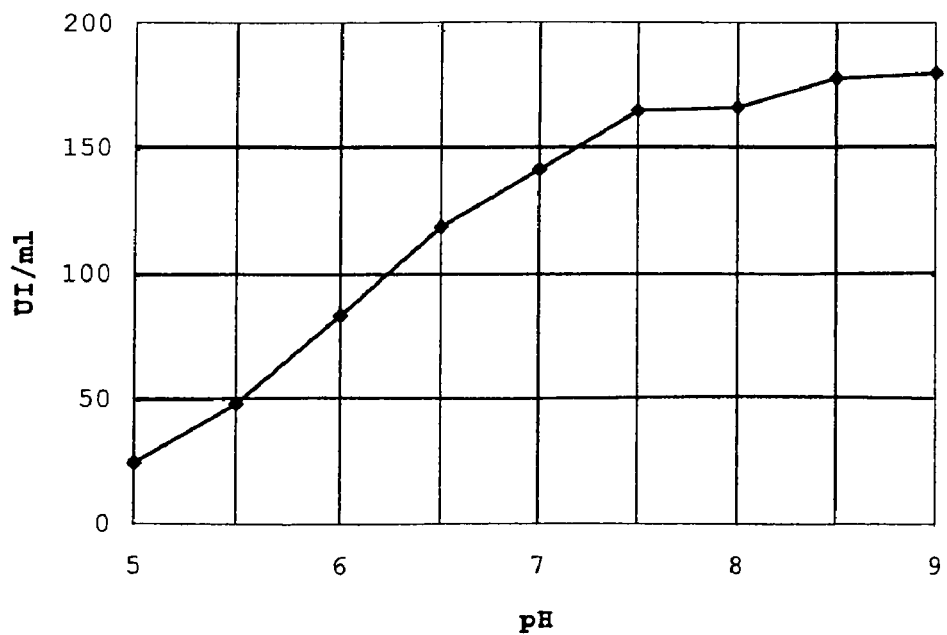
FIG. 2 Acetylesterase activity as a function of pH.

The procedure described in Example 14 is followed, with solutions temperature controlled at +25° C., maintaining the pH constant by automatic titration at values between 5 and 9. The hydrolytic activity is calculated as described in Example 14, plotting the activity in IU/ml against the operating pH to obtain the curve of FIG. 2.

Example 16

Hydrolysis kinetics of 7-methoxy-cefalotin as a function of pH and temperature

A 200 g/l solution of 7-methoxy-cefalotin is prepared and hydrolyzed with acetyl xylan esterase from recombinant *B. pumilis* in *E. coli* as described in Example 6, but operating at pH from 5.0 to 9.0 and temperature from −10 to +35° C. In the case of temperatures below 0° C., 10 vol % of glycerin is added to the aqueous solution.

The reactions are conducted to termination, until a 7-methoxy-cefalotin residue of less than 1 g/l is obtained.

Figure 3:
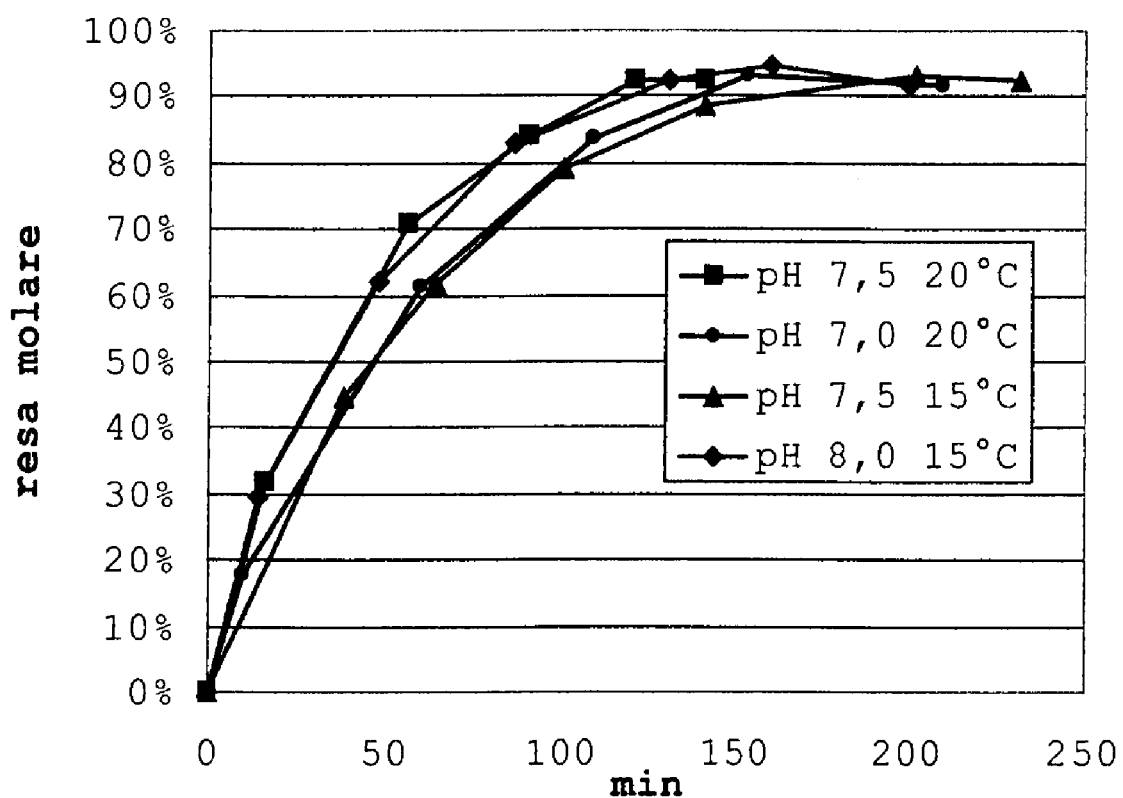
FIG. 3. Hydrolysis kinetics of 7-methoxy-cefalotin as function of pH and temperature.

FIG. 3 shows just some of the reaction kinetics. The product yields and quantities obtainable are influenced by possible product degradation, depending on the reaction conditions.

Example 17

Hydrolysis of 7-methoxy-cefalotin with immobilized acetyl esterase

The procedure described in Example 5 is followed, using acetyl esterase immobilized on resin as described in Examples from 5 to 7 and operating at pH 5, at +35° C. On termination of the reaction the agitation is halted and the catalyst allowed to decant, then the solution is separated by siphoning and the compound I is isolated as described in Example 11, to obtain 7-methoxy-3-desacetylcefalotin of titre 69%. A similar result is obtained operating at pH 9, at −10° C., adding 10% of glycerine to the aqueous solution.

Example 18

Synthesis of cefoxitin from 7-methoxy-3-desacetylcefalotin

Two samples of 7-methoxy-3-desacetylcefalotin benzathine salt obtained by the procedure described in Example 1 (sample A) and Example 12 (sample B) are transformed into cefoxitin by reaction with chlorosulphonyl isocyanate, as described for example in WO2004/083217A1. An identical molar yield is obtained.

The invention claimed is:
1. A process for preparing the compound of formula I:

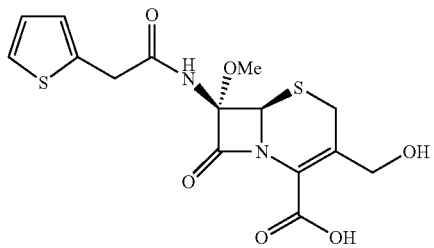

in which the compound of formula II:

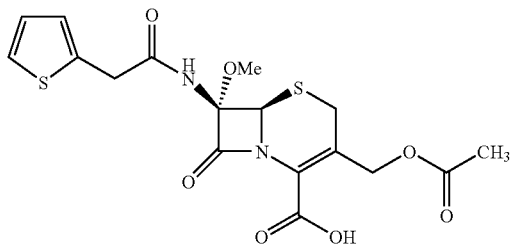

is subjected to hydrolysis of the acetyl group, wherein said hydrolysis is conducted in water in the presence of a catalyst consisting of at least one enzyme obtained from *Bacillus pumilus* possessing acetyl hydrolasic activity, thus forming an aqueous reaction medium, at a temperature between 0° C. and +20° C. and at a pH between 6 and 8.

2. The process as claimed in claim 1, wherein said catalyst consists of said at least one enzyme immobilized on a solid support.

3. The process as claimed in claim 1, further comprising isolating a salt of an organic base of said compound of formula I from the aqueous reaction medium by precipitation of said compound of formula I as the salt of benzathine.

4. The process as claimed in claim 1, wherein said hydrolysis temperature is between +15° C. and +20° C. and said pH is between 7.5 and 8.

5. A process comprising:
(1) subjecting the compound of formula II:

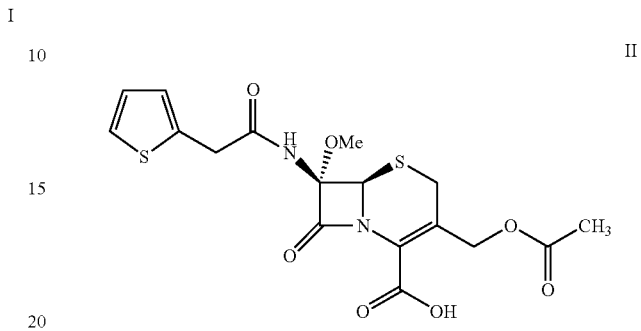

to hydrolysis of the acetyl group to produce the compound of formula I:

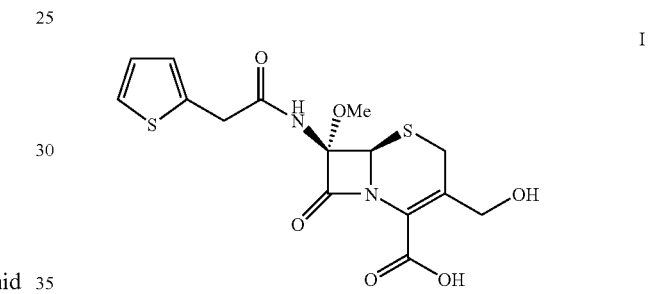

wherein said hydrolysis is conducted in water in the presence of a catalyst consisting of at least one enzyme obtained from *Bacillus pumilus* possessing acetyl hydrolasic activity, thus forming an aqueous reaction medium, at a temperature between 0° C. and +20° C. and at pH between 6 and 8; and
(2) isolating the compound of formula I by extracting the aqueous reaction medium with a solvent.

* * * * *